United States Patent [19]

Moyle

[11] 3,944,498
[45] Mar. 16, 1976

[54] GERMICIDAL DETERGENT CONTAINING A THIENYLIODONIUM SALT

[75] Inventor: Clarence L. Moyle, Clare, Mich.

[73] Assignee: The Dow Chemical Company, Midland, Mich.

[22] Filed: Nov. 30, 1973

[21] Appl. No.: 420,429

Related U.S. Application Data

[60] Continuation-in-part of Ser. No. 265,395, June 22, 1972, Pat. No. 3,763,187, which is a continuation-in-part of Ser. No. 154,182, June 17, 1971, abandoned, which is a continuation-in-part of Ser. No. 806,739, March 12, 1969, abandoned, which is a continuation-in-part of Ser. No. 677,772, Oct. 24, 1967, abandoned, Division of Ser. No. 323,977, Jan. 15, 1973, Pat. No. 3,885,036.

[52] U.S. Cl................................. 252/106; 252/107
[51] Int. Cl.$^2$........................ C11D 3/48; C11D 9/50
[58] Field of Search ............ 252/106, 107; 424/275; 260/332.3 R

[56] References Cited
UNITED STATES PATENTS

3,207,660 9/1965 Cannon............................... 260/612
3,422,152 1/1969 Doub................................. 260/612

*Primary Examiner*—P. E. Willis, Jr.
*Attorney, Agent, or Firm*—Theodore Post; C. Kenneth Bjork

[57] ABSTRACT

The present invention is concerned with novel antimicrobial thienyliodonium salts and methods and compositions employing the same, and is particularly directed to a class of thienyliodonium salts which are of value as antimicrobials and microbicides for the control of many bacterial organisms such as the gram-negative and gram-positive types, the molds, the mildews, the fungi and the slimes, and are of particular value for the preservation of paper, plaster, wallboards, fabric, textiles, cooling waters, plasticizers, latices, polymers, resins, adhesives, inks, paints, fuels, cutting oils, greases, seeds, terrestrial plants, detergents, soaps, shampoos and wood.

2 Claims, No Drawings

GERMICIDAL DETERGENT CONTAINING A THIENYLIODONIUM SALT

This is a division of application Ser. No. 323,977, filed Jan. 15, 1973, now U.S. Pat. No. 3,885,036.

This application is a continuation-in-part of U.S. patent application Ser. No. 265,395, filed June 22, 1972 now U.S. Pat. No. 3,763,187 which latter is a continuation-in-part of U.S. patent application Ser. No. 154,182, filed June 17, 1971, abandoned which latter is a continuation-in-part of U.S. patent application Ser. No. 806,739, filed Mar. 12, 1969 abandoned, the latter being a continuation-in-part of U.S. patent application Ser. No. 677,772, filed Oct. 24, 1967, abandoned.

BACKGROUND OF THE INVENTION

Many chemical materials have been proposed as valuable as antimicrobials and as preservatives. However, the materials heretofore proposed usually have been restricted in their scope of utility by virtue of one or more shortcomings such as low toxicity to bacterial organisms, toxicity to a relatively few types of organisms, toxicity to gram-positive types but not to gram-negative types of bacterial organisms, unfavorable toxicity to aquatic or terrestrial plants, unfavorable toxicity to mammals and lack of toxicity in the presence of detergents or soaps. The present compounds and methods wherein they are employed as microbicides are believed to have a particular combination of properties; namely, low toxicity to fish, mammals and terrestrial plants and plant parts, and high toxicity to microbes including both gram-negative and gram-positive types in many environments including soaps and detergents such as the fatty acid, anionic, and non-ionic soaps and detergents. A further advantage relates to the instability of the compounds under substantially alkaline aqueous conditions whereby the compounds have a tendency to break down and are thus degradable.

SUMMARY OF THE INVENTION

The novel compounds of the present invention are thienyliodonium salts corresponding to the following formula:

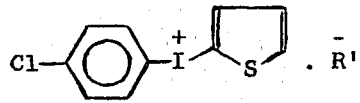

wherein R' represents chloride, trifluoroacetate or trichloroacetate. These compounds are crystalline solid materials which are somewhat soluble in many common organic solvents and in water.

The invention further provides the method which comprises treating microbes in inanimate, plant and external animal habitats with an antimicrobial amount of such a 2-thienyliodonium salt. The invention further provides germicidal detergents comprising an antimicrobial amount of a 4-chlorophenyl-2-thienyliodonium salt, as defined above.

The compounds have been found to be of high toxicity to many bacterial organisms or plants including gram-negative and gram-positive types, such as *S. aureus*, *S. typhose*, *B. subtilis*, *E. coli*, *P. aeruginosa*, *C. pelliculosa*, *A. terreus*, *A. aerogenes*, *P. chrysogenum*, *A. niger*, *C. globosum*, *P. digitatum*, *P. citri*, *D. natalensis*, *A. solani*, *E. amylovora* or *R. solani*. The compounds are of low toxicity to terrestrial plants and may be applied to many bacterial plants and their habitats in bactericidal amounts to obtain excellent controls of the microbial organisms which attack the seeds, roots or above-ground portions of terrestrial plants. Such practice protects the terrestrial plants and seeds and improves crop yield and the emergence and growth of seedlings. In further operations, it has been found that the compounds may be included in adhesives, cooling waters, inks, plasticizers, latices, resinous polymeric materials, fuels, greases, soaps, detergents, shampoos, cutting oils and oil or latex paints to prevent mold and mildew and the degradation of such products resulting from microbial attack. By resinous polymeric materials is meant natural and synthetic resinous polymers and plastic compositions or films derived therefrom. Also, the compounds advantageously may be distributed in natural and synthetic fabrics, and paper or other cellulosic products, or may be employed in the impregnation of wood, lumber, wallboard, and plaster to protect such products from the attack of the bacterial organisms of rot, mold, mildew and decay.

The thienyliodonium trifluoroacetate can be prepared by reacting together trifluoroacetic acid, thiophene, and 4-chloroiodosobenzene diacetate having the formula:

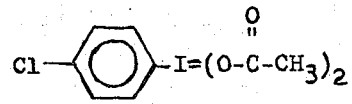

The reaction is preferably carried out in an organic liquid such as methylene chloride, ethylene dichloride, carbon tetrachloride, methylchloroform, heptane, or methylcyclohexane, and conveniently in acetic anhydride or in a mixture of acetic anhydride and trifluoroacetic acid. The reaction goes forward when the reagents are employed in any amounts. The reaction consumes the reagents in substantially equimolecular amounts and the employment of amounts which represent about equimolecular proportions is preferred. The reaction proceeds under temperatures from −30° to 40°C. and is preferably carried out at temperatures of from −20° to 40°C. Upon completion of the reaction, the desired 4-chlorophenyl-2-thienyliodonium trifluoroacetate is separated by conventional procedures.

In a convenient method of carrying out the reaction, the trifluoroacetic acid and iodosodiacetate are brought together in the reaction medium and the thiophene reagent added portionwise thereto with agitation. The reaction is exothermic and goes forward readily with the addition of the thiophene. The temperature of the reaction mixture can be controlled by regulating the rate of the addition of thiophene and by external cooling. The reaction essentially is complete upon completion of the addition of the thiophene. Allowing the resulting mixture to stand for a period of time at somewhat elevated temperatures oftentimes gives some improvement in yield. Upon completion of the reaction, the reaction mixture may be distilled under reduced pressure to remove a portion of the low boiling constituents and obtain the desired 4- chlorophenyl-2-thienyliodonium trifluoroacetate as a crystalline residue. This residue may be further purified by crystallization from organic solvents or aqueous organic solvents such as acetone, ethyl acetate, heptane or mixtures thereof.

The corresponding trichloroacetate is prepared by substituting trichloroacetic acid in place of trifluoroacetic acid in the procedure described above.

The corresponding chloride can be prepared from the 4-chlorophenyl-2-thienyliodonium trifluoroacetate by treatment of said trifluoroacetate with gaseous or aqueous hydrogen chloride. The reaction of the trifluoroacetate with the hydrogen chloride preferably is carried out in a liquid reaction medium, conveniently in acetone or ethyl acetate. The amounts of the reagents to be employed are not critical, some of the desired thienyliodonium chloride being obtained when employing the reagents in any proportions. However, the reaction consumes the reagents in substantially equimolecular proportions and the use of the reagents in amounts which represent such proportions is preferred. The reaction takes place readily at temperatures of from 0° to 50°C. with the production of the 4-chlorophenyl-2-thienyliodonium chloride and trifluoroacetic acid. During the reaction, the chloride salt usually precipitates in the reaction mixture as a crystalline solid. Following the reaction, the reaction mixture may be distilled under reduced pressure to remove low boiling constituents and bring about precipitation of the desired salt product. The 4-chlorophenyl-2-thienyliodonium chloride so prepared may be separated by decantation or filtration, and further purified by recrystallization from various organic solvents or aqueous organic solvents such as acetone, ethyl acetate, normalpentane, heptane or mixtures thereof.

The iodosodiacetate employed as a starting material as herein described can be prepared in accordance with known methods. In such methods, 4-chloroiodobenzene dichloride is reacted with lead acetate ($CH_3COO$-$Pb$-$OOCCH_3$). The reaction takes place readily at room temperature with the production of the desired diacetate and lead chloride. The dichloride employed in such mechanism is conveniently prepared in a known procedure by the chlorination of 4-chloroiodobenzene.

In an alternative procedure, the 4-chloroiodosobenzene diacetate can be prepared by reacting the 4-chloroiodobenzene with peracetic acid in acetic acid and acetic anhydride solution. This reaction conveniently is carried out at room temperature. In these reaction, 4-chloroiodosobenzene diacetate, the desired product, is isolated as a crystalline solid and is separated and purified in accordance with known procedures.

Good controls of microbes can be obtained when the toxicant compounds are applied to the above-ground portions of terrestrial plants at a dosage of from 1 to 10 or more pounds per acre (1.12–11.2 kg./hectare). In applications to soil for the control of root-attacking microbes, good results are obtained when the salt compounds are distributed at a rate of from 10 to 100 pounds or more per acre (11.2–112 kg/hectare). In general field applications, it is usually preferred that the compounds be distributed to a depth of at least 2 inches (5 cm.) below the soil surfaces.

In the protection and preservation of inks, adhesives, soaps, detergents, greases, fuels, cutting oils, textiles, fabrics, latices, resinous plasticizers, polymeric materials and paper, good results are obtained when the compounds are incorporated in such products in the amount of at least 0.0005 percent by weight. In the protection of seeds, good results are obtained when the seeds are treated with the compounds at a dosage of 0.5 ounce per 100 pounds of seed (0.03 weight percent based on weight of seed). In the preservation of wood, wallboard and plaster, excellent results are obtained when the compounds are incorporated by conventional treatment of these products in the amount of 0.1 pound or more per cubic foot (0.0016 g./cc.) of product. In the treatment of fruit, good results are obtained with liquid washes containing at least 5 parts per million by weight of salt compound.

In the preservation and protection of oil and latex paints and primers against destruction caused by the growth of bacteria, the compounds are preferably employed at concentrations of at least 0.05 percent by weight.

The method of the present invention can be carried out employing unmodified compounds or by employment of liquid or dust compositions containing the toxicants. In such usage, the compounds are modified with one or a plurality of additaments or adjuvants including water, organic solvents, petroleum oils, petroleum distillates, naphthas or other liquid carriers, polymeric thickening agents, urea, surface-active dispersing agents and finely divided inert solids. In compositions wherein the adjuvant or helper is a finely divided solid, a surface-active agent or the combination of a surface-active agent and a liquid diluent, the carrier cooperates with the active component so as to facilitate the invention and to obtain an improved result.

The exact concentration of the toxicants to be employed in the treating compositions is not critical and may vary considerably provided the required dosage of the effective agent is supplied. The concentration of toxicant in liquid compositions generally is from 0.0001 to 50 percent by weight. Concentrations up to 95 percent by weight are oftentimes conveniently employed. In dusts, the concentrations of the toxicant can be from about 0.1 to 95 percent by weight. In compositions to be employed as concentrates, the toxicants can be present in a concentration of from 5 to 98 percent by weight.

In further embodiments, the salt compounds as employed in accordance with the present invention, or compositions containing the same, can be advantageously employed in the present invention in combination with one or more pesticidal or preservative compounds to obtain products of enhanced properties. In such embodiments, such pesticidal or preservative compounds are employed either as a supplemental toxicant, an additament or as an adjuvant. Representative pesticidal or preservative compounds include substituted phenols, cresols, substituted cresols and their heavy metal salts, bisphenols and thiobisphenols; halogenated salicylanilides, organosulfur compounds, carbamate compounds, quaternary ammonium compounds, organometallic compounds, inorganic salts and miscellaneous other compounds such as phenol; cresol; trichlorophenols; tetrachlorophenols; pentachlorophenol; p-chloro-m-cresol; di- and tribrominated salicylanilides; 2,2'-methylene-bis(3,4,6-trichlorophenol); 2,2'-thiobis(4,6-dichlorophenol); 1-(3-chloroallyl)-3,5,7-triaza-1-azoniaadamantane chloride; halo(alkylsulfonyl)-pyridines; halo(alkylsulfinyl)pyridines; 2,4',5-tribromosalicylanilide; 2-chloro-4-cyclohexylphenol; 2-chloro-4-cyclopentylphenol; 2,2'- bis(3,4,6-trichlorophenyl)methane; 2,2'-bis(5-chloro-2-hydroxyphenyl)methane; halogenated trifluoromethyl salicylanilide; zinc dimethyldithiocarbamate; 2-mercaptobenzothiazole; 3,5-dimethyltetrahydro-1,3,5,2H-thiadiazine-2-thione; 2,3-dinitro-1,4-dithiaanthraquinone; dodecyl pyridinium chloride; alkyl dimethyl benzyl ammonium chloride; dialkyl dimethyl ammonium chloride; phenylmercuric acetate; phenyl mercuric oleate; phenylmercuric propionate; chloromethoxy acetoxy mercuripropane; bis-tributyl tin oxide; bix-tripropyl tin oxide; copper pentachlorophenate; copper 8-hydroxyquinolate; mercuric chloride; boric acid; sodium borate; ethylmercuric chloride; 9-undecylenic acid; or 10,10'-oxybisphenoxarsine and 1,4-bromobisacetobutene.

DESCRIPTION OF SOME PREFERRED EMBODIMENTS

EXAMPLE 1

4-Chlorophenyl-2-thienyliodonium trifluoroacetate

4-Chloroiodosobenzene diacetate (17.3 grams; 0.05 mole) was dispersed in a mixture of 15 milliliters each of acetic anhydride and trifluoroacetic acid, and a solution of thiophene (8.4 grams; 0.10 mole) in 60 milliliters of acetic anhydride added slowly thereto. The addition was carried out with stirring in 55 minutes at $-20°C$. Stirring was continued for 65 minutes at $-20°C$., and the reaction mixture thereafter warmed and maintained at $-3°C$. with stirring for 15 hours to insure completion of the reaction. The reaction mixture was concentrated by fractional distillation under reduced pressure up to $50°C$., and the resulting residue diluted with 100 milliliters of diethyl ether. During the dilution, the 4-chlorophenyl-2-thienyliodonium trifluoroacetate precipitated as a crystalline solid and was separated by filtration. The solid, recrystallized from a mixture of acetone and normal pentane, melted at $156°-157.5°C$.

EXAMPLE 2

4-Chlorophenyl-2-thienyliodonium chloride

4-Chlorophenyl-2-thienyliodonium trifluoroacetate (7 grams; 0.0161 mole) was dispersed in 8 milliliters of an 88 percent by weight solution of formic acid in water, and a saturated aqueous solution of hydrogen chloride (12 milliliters) added thereto at room temperature with stirring. During the addition, 4-chlorophenyl-2-thienyliodonium chloride precipitated as a crystalline solid and was filtered, washed with ether and water, and twice recrystallized from ethanol. The product melted at $217°-218°C$.

EXAMPLE 3

The 4-chlorophenyl-2-thienyliodonium chloride, trifluoroacetate and trichloroacetate salts are dispersed in melted nutrient agar to produce culture media containing 0.001 percent by weight of one of the salt compounds. Such melted media are then poured into petri dishes and the solidified surface in each dish inoculated with a 24-hour broth culture, one of the organisms *S. aureus* and *S. typhosa*. In a check operation, petri dishes containing unmodified nutrient agar are each individually inoculated in the same manner with the named organisms. After two days' incubation at $35°C$. the agar surface in each dish is examined for microbial growth. The examination shows that the agar surface in the dishes containing the thienyliodonium salts is free of microbial growth. At the time of these observations the check dishes are found to support a heavy growth of the two named organisms.

EXAMPLE 4

4-Chlorophenyl-2-thienyliodonium chloride is employed in a paint composition to protect the paint from attack and subsequent degradation by the organisms of mold and mildew. In such operations, the salt compound is dispersed and incorporated in the latex paint in the amount of 0.3 percent by weight of the ultimate paint composition.

The paint employed in these operations is prepared by intimately blending a pigment dispersion with a letdown including a synthetic latex comprising an interpolymer of ethyl acrylate, methyl methacrylate, acrylic acid and methacrylic acid. The paint has the following composition.

| Pigment dispersion: | Approximate lbs. per 100 gallons (g./l.) | |
|---|---|---|
| Water | 140 | (168) |
| Potassium tripolyphosphate | 1.5 | (1.8) |
| Titanium dioxide | 240 | (288) |
| Mica (325 mesh) | 50 | (60) |
| Calcium carbonate | 20 | (24) |
| Clay (finely ground) | 20 | (24) |
| Propylene glycol (mol. wt. 1200) | 4 | (4.8) |
| Let down: | Approximate lbs. per 100 gallons(g./l.) | |
| Methyl cellulose | 150 | (180) |
| Synthetic latex | 506 | (607) |
| Anti-foam agent | 10 | (12) |

Wood panels are then painted with the modified compositions as well as with the unmodified paint. The panels are dried and thereafter exposed two months in a tropical chamber at a relative humidity of 95 percent and a temperature of $82°F$. ($28°C$.). Following this period, the wood panels are examined to ascertain what control of plant growth is obtained. The examination shows a complete control of the growth of the organisms of mold and mildew.

At the time of the observation, the check panels painted with the unmodified composition are found to support a heavy growth of the organisms of mold and mildew covering approximately 75 percent of the painted surfaces.

EXAMPLE 5

Phenyl-2-thienyliodonium chloride, 2,2'-bisthienyliodonium chloride, and, for comparative purposes, diphenyliodonium chloride are individually dispersed in Ivory soap to provide concentrates containing 1 part by weight of iodonium salt to 50 parts by weight of soap. The soap concentrates are serially dispersed and serially diluted with liquid nutrient agar at $42°C$. to prepare culture media containing various concentrations of one of the iodonium salts. The culture media are uniformly inoculated with *S. aureus* and plated in petri dishes. The inoculation is carried out from broth cultures of the named organism containing about $5 \times 10^8$ organisms per milliliter in the proportion of one-tenth milliliter of bacterial culture per 20 milliliters of cultur medium containing each test compound. In a check operation, nutrient agar containing the same amount of Ivory soap is similarly inoculated with the same organism. After two days' incubation at $37°C$., the plates are examined for microbial growth. The examination shows that the plates containing 2.5 parts per million, p.p.m., by weight of phenyl-2-thienyliodonium chloride and 5 parts per million by weight of 2,2'-bisthienyliodonium chloride are completely free of bacterial growth (referred to as 100 percent kill in Tables) of *S. aureus* while the plates containing 500 parts per million by weight of diphenyliodonium chloride and the check plates containing no iodonium salt are found to have a heavy uniform growth of the test organism.

The procedure described above is repeated with varying concentrations of 4-chlorophenyl-2-thienyliodonium chloride, 3,4-dichlorophenyl-2-thienyliodonium chloride, and for comparative purposes bis(4-chlorophenyl)iodonium chloride, phenyl-4-chlorophenyliodonium chloride and bis(2,4-dichlorophenyl)iodonium chloride in a series of tests wherein the culture media are inoculated individually with the organism *A. aerogenes*. The results obtained are summarized in following Table I.

TABLE I

| Thienyl Compound | Concentration (p.p.m.) | Percent Kill of A. aerogenes |
| --- | --- | --- |
| 4-chlorophenyl-2-thienyl-iodonium chloride | 1 | 100 |
| 3,4-dichlorophenyl-2-thienyliodonium chloride | 1 | 100 |
| For comparison | | |
| bis(4-chlorophenyl)iodonium chloride | 100 | 0 |
| phenyl-4-chlorophenyl-iodonium chloride | 10 | 0 |
| bis(2,4-dichlorophenyl)-iodonium chloride | 10 | 0 |

The procedure described above is again repeated in a series of tests wherein the culture media are inoculated individually with the organism *S. typhosa* and wherein the culture media contain varying concentrations of one of the iodonium salts, as set forth in following Table II. The plates upon examination exhibit results summarized in Table II.

TABLE II

| Thienyl Compound | Concentration (p.p.m.) | Percent Kill of S. Typhosa |
| --- | --- | --- |
| 2,2'-bisthienyliodonium chloride | 5 | 100 |
| phenyl-2-thienyliodonium chloride | 2.5 | 100 |
| 4-chlorophenyl-2-thienyl-iodonium chloride | 1 | 100 |
| 4-bromophenyl-2-thienyl-iodonium chloride | 5 | 100 |
| 3,4-dichlorophenyl-2-thienyliodonium chloride | 1 | 100 |
| For comparison | | |
| diphenyliodonium chloride | 500 | 0 |
| phenyl-4-chlorophenyl-iodonium chloride | 10 | 0 |
| bis(4-bromophenyl)-iodonium chloride | 10 | 0 |
| bis(4-bromophenyl)iodonium bromide | 10 | 0 |
| bis(2,4-dichlorophenyl)-iodonium chloride | 10 | 0 |

The procedure described above is once again repeated with each of 2,2'-bisthienyliodonium chloride, phenyl-2-thienyliodonium chloride, 4-bromophenyl-2-thienyliodonium chloride, bis(4-bromophenyl)iodonium chloride and bis(4-bromophenyl)iodonium bromide in a series of tests wherein the culture media are inoculated individually with the organism *A. aerogenes*. The results obtained are summarized in following Table III.

TABLE III

| Thienyl Compound | Concentration (p.p.m.) | Percent Kill of A. aerogenes |
| --- | --- | --- |
| 2,2'-bisthienyliodonium chloride | 5 | 100 |
| phenyl-2-thienyliodonium chloride | 2.5 | 100 |
| 4-bromophenyl-2-thienyl-iodonium chloride | 5 | 100 |
| For comparison | | |
| bis(4-bromophenyl) iodonium chloride | 10 | 0 |
| bis(4-bromophenyl)iodonium bromide | 10 | 0 |

EXAMPLE 6

A germicidal shampoo is prepared having the following weight percent composition:

A. thienyliodonium salt 2
B. 95% ethanol 2
C. triethanolamine ammonium lauryl sulfate 19.0
D. oleic diethanolamide 3.2
E. lauric isopropanolamide 1.7
F. water 72.1

F is added to a mixture of C, D and E with stirring to form a clear solution, and to the resulting solution is added a slurry of A in B with continued stirring to form a clear solution. Any of the thienyliodonium salts disclosed in Example 3 is used as ingredient A.

EXAMPLE 7

Two parts by weight of each of the thienyliodonium salt compounds identified in Example 3 is separately mixed and ground with 98 weight parts of a soap or nonionic detergent powder to give germicidal detergent compositions. By "detergent" is meant an anionic or non-ionic detergent i.e., a fatty acid soap or a non-ionic syndet soap or a mixture of fatty acid and non-ionic syndets.

EXAMPLE 8

The growth-inhibitory activity of the below-indicated compounds against some microorganisms most relevant to the human skin was determined by standard agar dilution techniques to provide the data given in following Table 1.

TABLE 1

A. ANTIMICROBIAL ACTIVITY IN THE PRESENCE OF IVORY SOAP

| Compound | Minimum growth inhibitory concentration, ppm | | |
|---|---|---|---|
| | S. aureus | P. aeruginosa | S. typhosa |
| 1. (phenyl)$_2$I$^\oplus$ Cl$^\ominus$ | >500 | >500 | >500 |
| 2. phenyl-I$^\oplus$-thienyl Cl$^\ominus$ | 5 | 5 | 5 |
| 3. (thienyl)$_2$I$^\oplus$ Cl$^\ominus$ | 0.5 | 5 | 0.5 |
| 4. (4-Cl-phenyl)-I$^\oplus$-phenyl Cl$^\ominus$ | 10 | >100 | >10 |
| 5. (4-Cl-phenyl)$_2$I$^\oplus$ Cl$^\ominus$ "Iodonium 235" | 10 | >100 | 10 |
| 6. (4-Cl-phenyl)-I$^\oplus$-thienyl Cl$^\ominus$ | 1 | 1 | 1 |
| 7. (3,4-di-Cl-phenyl)$_2$I$^\oplus$ Cl$^\ominus$ | 5 | >500 | >10 |
| 8. (3,4-di-Cl-phenyl)-I$^\oplus$-thienyl Cl$^\ominus$ | 1 | 1 | 1 |

TABLE 1-continued

A. ANTIMICROBIAL ACTIVITY IN THE PRESENCE OF IVORY SOAP

| Compound | Minimum growth inhibitory concentration, ppm | | |
|---|---|---|---|
| | S. aureus | P. aeruginosa | S. typhosa |
| 9. (4-ethoxyphenyl)(phenyl)iodonium chloride | >500 | >500 | >500 |
| 10. (4-ethoxyphenyl)(2-thienyl)iodonium chloride | 5 | 50 | 5 |

B. ANTIMICROBIAL ACTIVITY IN THE ABSENCE OF SOAP

| Compound | Minimum growth inhibitor concentration, ppm | | |
|---|---|---|---|
| | S. aureus | P. aeruginosa | S. typhosa |
| 11. (3-trifluoromethylphenyl)(4-methoxyphenyl)iodonium chloride | 10 | 500 | 100 |
| 12. (3-trifluoromethylphenyl)(2-thienyl)iodonium chloride | <1 | 50 | 10 |
| 13. dibenziodolium lactate (*Lac = lactate) | 3.13 | 3.13 | — |
| 14. dibenziodolium sulfate (SO$_4^{2-}$/2) | 5 | 5 | — |
| 15. chloro-dibenziodolium sulfate (SO$_4^{2-}$/2) | 1.56 | 3.13 | — |

TABLE 1-continued
A. ANTIMICROBIAL ACTIVITY IN THE PRESENCE OF IVORY SOAP

| Compound | Minimum growth inhibitory concentration, ppm | | |
|---|---|---|---|
| | S. aureus | P. aeruginosa | S. typhosa |
| 16. (diphenyliodonium sulfate, dichloro) | 1.56 | 6.25 | — |
| 17. Merthiolate® | <1 | 1 | <1 |
| 18. Irgasan® | 1 | >300 | 1 |

In Table 1, the first column gives the chemical structures of the test compounds, while the additional columns give the names of the test organisms and the minimum inhibitory concentration in parts per million (p.p.m.) of the compounds listed for 100% growth inhibition against the particular microorganisms indicated. A dash indicates that the compound was not tested against that organism. For each p.p.m. of test compound, 50 p.p.m. of Ivory soap was also present in the culture medium for part A of Table 1, while in part B of Table 1, the culture medium was free of any additive other than the test compound. The data for compounds 13 through 16 of part B of Table 1 were taken from Cannon U.S. Pat. No. 3,207,660 while those for compounds 17 and 18 were taken from trade literature.

The data show a difference in kind in antimicrobial activity for the thienyliodonium compounds when compared with diphenyl- and substituted diphenyliodonium compounds known to have some antimicrobial activity and closest in structure to the thienyliodonium compounds. Also, the data show no substantial difference as between culture media containing Ivory soap and not containing Ivory soap.

The antimicrobial effectiveness against *P. aeruginosa* (*Pseudomonas aeruginosa* or *Pseudomonas*) of the thienyliodonium salts is noteworthy. This organism is considered one of the most dangerous pathogens and is responsible for the constantly increasing number of hospital cross infections caused by gram-negative bacteria in the last decade. See, for example "Disinfection", M. A. Benarde, Ed., Marcel Dekker, Inc., New York, N.Y., 1970, 260–263 and "Inhibition and Destruction of the Microbial Cell", W. B. Hugo, Ed., Academic Press, New York, N.Y., 1971, 330–333.

EXAMPLE 9

The range-finding oral median lethal dose ($LD_{50}$) for iodonium and other antimicrobial compounds, including diphenyl- and thienyliodonium salts as well as several proprietary products was determined in mice. Compounds 1 through 11 of following Table 2 were fed to five groups of two mice each, the test compound being administered in suspension in corn oil as a single oral dose and the mortality experience of the mice was observed over a 14-day period. Data for compounds 12 through 15 were taken from U.S. Pat. No. 3,207,660, and for compounds 16 through 18 were taken from trade literature.

Table 2
COMPARISON OF ORAL MEDIAN LETHAL DOSE ($LD_{50}$) OF IODONIUM SALTS AND PROPRIETARY ANTIMICROBIALS
| Compound | TOXICITY Oral $LD_{50}$ (mice) mg/kg |
|---|---|
| 1. 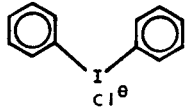 | 56.2 |
| 2. 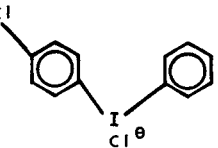 | 68 |
| 3. 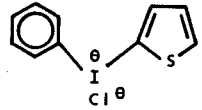 | 2000 |
| 4. 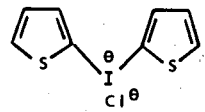 | 500 |
| 5. 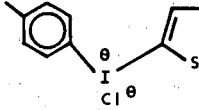 | >4000 |
| 6. 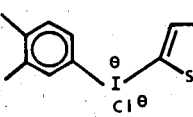 | 2000 |
| 7. 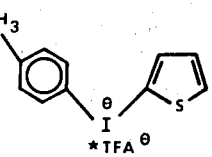 | 750 |
| 8. 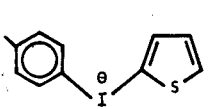 | 1500 |

Table 2-continued
COMPARISON OF ORAL MEDIAN LETHAL DOSE (LD$_{50}$) OF IODONIUM SALTS AND PROPRIETARY ANTIMICROBIALS
| | Compound | TOXICITY Oral LD$_{50}$ (mice) mg/kg |
|---|---|---|
| 9. | 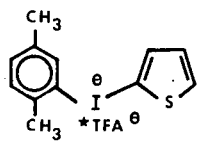 | 3000 |
| 10. | 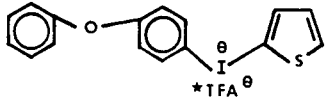 | 3000 |
| 11. | 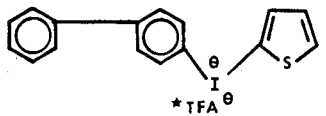 | 4000 |
| 12. | 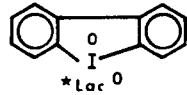 | 12.5 |
| 13. | 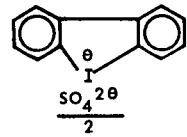 | 8.75±0.57 |
| 14. | 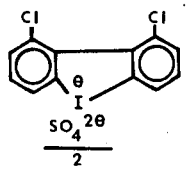 | 8–10 |
| 15. | 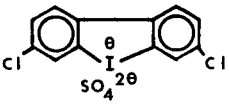 | 21.32±3.2 |
| 16. | 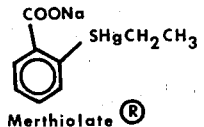 Merthiolate® | 66 (S.C.)* |
| 17. | 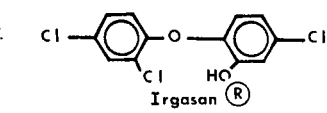 Irgasan® | 4000 |

Table 2-continued

COMPARISON OF ORAL MEDIAN LETHAL DOSE ($LD_{50}$) OF IODONIUM SALTS AND PROPRIETARY ANTIMICROBIALS

| Compound | TOXICITY Oral $LD_{50}$ (mice) mg/kg |
|---|---|
| 18. 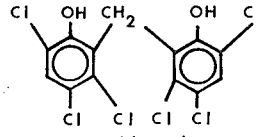 Hexachlorophene | 161 |

*TFA=trifluoroacetate
*S. C.=subcutaneous

Table 2 shows that whereas (p-chlorophenyl)(phenyliodonium)chloride, is shown in Table 1 to be one of the more effective antimicrobials of the diphenyliodonium type, it has a low and undesirable $LD_{50}$ of 68 mg/kg in mice. The antimicrobial iodolium etc. compounds of Cannon U.S. Pat. No. 3,207,660 have even lower $LD_{50}$ values, ranging between 8 and 21.32 ± 3.2 mg/kg in mice. Of the proprietary compounds, Merthiolate has an $LD_{50}$ of 66 subcutaneously and hexachlorophene has an oral $LD_{50}$ of 161. Irgasan antimicrobial, having a reported $LD_{50}$ of 4,000 mg/kg in mice, has a minimum growth inhibiting concentration of more than 300 ppm against P. aeruginosa. The thienyliodonium antimicrobials are more effective and have desirably high $LD_{50}$ values of 500 to more than 4,000, as shown.

EXAMPLE 10

Based on the screening data reported above, which showed for the thienyliodonium salts in general a high level of antimicrobial activity against gram-positive and gram-negative bacteria coupled with a desirable low level of toxicity additional tests were carried out for the representative compound p-chlorophenyl-2-thienyliodonium chloride, hereinafter referred to as "ClPhThICl", as follows. Conventional serial dilution tests for inhibitory activity of the said compound against a plurality of gram-positive and gram-negative bacteria, fungi and yeasts were carried out starting with the following formulations.

I: 0.1% ClPhThICL: 5.0 gms of dried powdered Dove soap (coconut oil acid ester of sodium isethionate) in 94.9 ml. of water.

II: 0.25% ClPhThICl: 55% Varifoam YM (modified alcohol sulfate, 38% active), 0.1% citric acid in 44% water. pH 5.5.

III: 0.125% ClPhThICl: 50% Tergitol 15-S-9, (polyglycol ether of linear alcohol, 100% active), 0.05% citric acid in 50% water. pH 2.2.

IV: 0.25% ClPhThICl in Touch of Sweden hand lotion, pH ca. 5.5.

V: 0.25% ClPhThICl: 0.1% citric acid in glycerin

VI: 0.25% ClPhThICl: 0.1% citric acid in ethanol

VII: 0.1% ClPhThICl: 0.1% citric acid in Dowanol DPM (dipropylene glycol monomethyl ether)

VIII: 0.1% ClPhThICl: in water

Formulations VI and VII were aged 3 weeks at room temperature before being tested for antimicrobial activity. The other compositions were not aged before testing.

Test Procedure: Initially, a stock solution in water for each formulation was prepared by dilution to contain 100 ppm ClPhThICl. From this 100 ppm stock solution, test agars were prepared by mixing appropriate amounts of the stock solution with a measured amount of sterile molten agar that had been cooled to 60°C. The treated molten agar was immediately mixed and poured into a sterile petri dish. Nutrient agar was used for testing bacteria and malt yeast agar for fungi and yeasts. In most cases, the test agars containing 10, 7.5, 5.0, 2.5, 1.0, 0.75 and 0.5 ppm of ClPhThICl were prepared from each formulation as described above. In the case of fungi and yeasts, a concentration of 50 ppm was also tested. Agars containing the formulation without the antimicrobial were also included at the appropriate levels to test the activity of the formulation.

The test cultures were applied to the surface of the hardened agar with a sterile cotton swab. A streak of about 1½ inches long was made. The inoculated plates were incubated for 48 hours at 30°C. Results in Table 3 are recorded as growth or no growth for the minimum concentration for 100% inhibition of growth. In all cases, the next lower concentration tested failed to inhibit growth of the microorganism completely. The blank spaces indicate that the formulation was not tested against the indicated microorganism.

Table 3

A: MINIMUM CONCENTRATION IN PPM OF ClPhThICl GIVING 100% INHIBITION OF BACTERIA

| Microorganism | I | II | III | IV | V | VI** | VII** | VIII |
|---|---|---|---|---|---|---|---|---|
| Staphylococcus aureus | 1.0 | * | <1.0 | 2.5 | 2.5 | 2.5 | 5.0 | 0.75 |
| Staphylococcus albus | 0.75 | <1.0 | 2.5 | 2.5 | <1.0 | | | 0.25 |
| Salmonella typhosa | <0.5 | <1.0 | * | <1.0 | <1.0 | 2.5 | 5.0 | 0.75 |
| Salmonella paratyphi | <0.5 | <1.0 | <1.0 | 2.5 | <1.0 | | | <0.5 |

Table 3-continued

A: MINIMUM CONCENTRATION IN PPM OF ClPhThICl GIVING 100% INHIBITION OF BACTERIA

| Microorganism | I | II | III | IV | V | VI** | VII** | VIII |
|---|---|---|---|---|---|---|---|---|
| Salmonella choleraseus | <0.5 | | | | | | | <0.5 |
| Bacillus subtilis | <0.5 | <1.0 | * | <1.0 | <1.0 | 1.0 | 1.0 | <0.5 |
| Bacillus mycoides | 1.0 | * | * | 2.5 | 2.5 | | | 2.5 |
| Bacillus megaterium | 1.0 | * | * | 2.5 | 2.5 | | | 2.5 |
| Pseudomonas aeruginosa | 0.75 | <1.0 | 5.0 | <1.0 | <1.0 | 5.0 | 5.0 | 0.75 |
| Pseudomonas spp PRD-10 | 1.0 | * | * | 2.5 | 2.5 | 2.5 | 2.5 | 2.5 |
| Pseudomonas fluorescens | 2.5 | 2.5 | 2.5 | 2.5 | 2.5 | | | <0.5 |
| Aerobacter aerogenes | 1.0 | 2.5 | 2.5 | 2.5 | 2.5 | 2.5 | 5.0 | 2.5 |
| Alcaligens faecales | 5.0 | 2.5 | 2.5 | 5.0 | 7.5 | 7.5 | 7.5 | 1.0 |
| Escherechia coli | 1.0 | 2.5 | 2.5 | 2.5 | 2.5 | 2.5 | 5.0 | 2.5 |
| Proteus vulgaris | 2.5 | * | 2.5 | 5.0 | 7.5 | | | 2.5 |
| Proteus mirabilis | 2.5 | <1.0 | <1.0 | 5.0 | 7.5 | | | |
| Proteus morginii | 1.0 | | | | | | | <0.5 |
| Flavobacteria arborescens | 2.5 | <1.0 | 2.5 | 5.0 | 5.0 | | | <0.5 |
| Micrococcus candidus | 2.5 | 2.5 | 2.5 | 5.0 | 10 | | | 1.0 |
| Sarcina lutea | 0.75 | * | * | 2.5 | 2.5 | | | |
| Brevibacterium ammoneagenes | 1.0 | * | * | 2.5 | 2.5 | | | 2.5 |
| Serratia marcescens | 2.5 | 5.0 | 5.0 | 2.5 | 2.5 | | | |
| Streptococcus mutans | * | | | <1.0 | <1.0 | | | |

*Formulation itself indicates activity at a concentration equivalent to the amount used which would contain 10 ppm of ClPhThICl.
**Formulations aged 3 weeks at room temperature before being tested.

B: MINIMUM CONCENTRATION IN PPM OF ClPhThICl GIVING 100% INHIBITION OF FUNGI AND YEAST

| Microorganism | I | IV | V |
|---|---|---|---|
| Saccharomyces cereviseae | >50 | 50 | 50 |
| Candida albicans | 5.0 | 50 | >50 |
| Candida pelliculosa | 10 | >50 | >50 |
| Trichophyton mentagrophytes | * | 50 | 50 |
| Aspergillus terreus | * | 50 | >50 |
| Pencillium chrysogenum | * | 50 | >50 |
| Pityrosporum ovale | 2.5 | 5.0 | 7.5 |
| Trichoderma spp | 10 | 50 | >50 |

*Formulation itself indicates activity at a concentration equivalent to the amount which would contain 50 ppm of ClPhThICl

EXAMPLE 11

Also, the oral median lethal dose, $LD_{50}$, was determined for ClPhThICl in Swiss mice (Cox strain) within a weight range of 16 to 22 grams. Five groups of mice, each consisting of 15 males and 15 females, were given ClPhThICl in an aqueous 0.5 percent METHOCEL hydroxypropyl methylcellulose (4000 cps.) suspension at a concentration of 300 mg/ml. The compound was administered as a single oral dose at 0.2 logarithmic dose intervals (708, 1120, 1780, 2820, 4450 mg/kg) and the following mortality experience was noted:

| Group | Dose (mg/kg) | No. Dead at 24 Hours Males | Females | No. Dead at 7 Days Males | Females | No. Dead at 14 Days Males | Females |
|---|---|---|---|---|---|---|---|
| 1 | 708 | 0/15 | 0/15 | 0/15 | 1/15 | 1/15 | 2/15 |
| 2 | 1120 | 0/15 | 0/15 | 1/15 | 1/15 | 1/15 | 2/15 |
| 3 | 1780 | 3/15 | 4/15 | 8/15 | 8/15 | 9/15 | 8/15 |
| 4 | 2820 | 11/15 | 8/15 | 14/15 | 14/15 | 14/15 | 14/15 |
| 5 | 4450 | 15/15 | 13/15 | 15/15 | 15/15 | 15/15 | 15/15 |

The percent of total mortalities occurring was 16.0, 66.6, 81.5, and 91.3 at 6, 24, 48 and 72 hours post-treatment, respectively. The last death occurred in a female (1120 mg/kg group) on day 14 of the study. $LD_{50}$ values and 95 percent confidence limits calculated at 24 hours, 7 and 14 days by the method of Litchfield-wilcoxon were as follows:

24 hours:
Male mice   2300 mg/kg   95% Confidence limits 1916–2760
Female mice   2700 mg/kg   95% Confidence limits 2300–3591 mg/kg 7 Days
Male mice   1760 mg/kg   95% Confidence limits 1353–2288 mg/kg
Female mice   1700 mg/kg   95% Confidence limits 1172–2455 mg/kg 14 Days
Male mice   1760 mg/kg   95% Confidence limits 1353–2288 mg/kg
Female mice   1580 mg/kg   95% Confidence limits 1264–1975 mg/kg The oral median lethal dose ($LD_{50}$) of ClPhThICl was also determined in Sprague-Dawley (Cox strain) rats within a weight range of 93 to 118 grams. Five groups of rats, each consisting of 10 males and 10 females, were given the compound in an aqueous 0.5 percent METHOCEL hydroxypropyl methylcellulose (4000 cps.) suspension at a concentration of 300 mg/ml. The compound was administered as a single oral dose at 0.2 logarithmic dose intervals (709, 1120, 1780, 2820, 4450 mg/kg), and the following mortality experience was noted:

| Group | Dose (mg/kg) | No. Dead at 24 Hours Males | No. Dead at 24 Hours Females | No. Dead at 7 Days Males | No. Dead at 7 Days Females | No. Dead at 14 Days Males | No. Dead at 14 Days Females |
|---|---|---|---|---|---|---|---|
| 1 | 708 | 1/10 | 0/10 | 1/10 | 0/10 | 1/10 | 0/10 |
| 2 | 1120 | 1/10 | 2/10 | 2/10 | 6/10 | 2/10 | 6/10 |
| 3 | 1780 | 4/10 | 6/10 | 9/10 | 7/10 | 9/10 | 7/10 |
| 4 | 2820 | 8/10 | 9/10 | 8/10 | 10/10 | 8/10 | 10/10 |
| 5 | 4450 | 9/10 | 10/10 | 10/10 | 10/10 | 10/10 | 10/10 |

The percent of total mortalities occurring was 53.9, 79.3, 85.7 and 93.6 at 6, 24, 48 and 72 hours post-treatment, respectively. The last death occurred between 72 and 96 hours post-treatment in male rats in the 1780 and 4450 mg/kg groups. $LD_{50}$ values and 95 percent confidence limits calculated at 24 hours, 7 and 14 days by the method of Litchfield-Wilcoxon were as follows:

24 Hours
Male rats    1800 mg/kg    95% Confidence limits 1241–2610 mg/kg
Female rats  1600 mg/kg    95% Confidence limits 1230–2080 mg/kg 7 and 14 Days
Male rats    1640 mg/kg    95% Confidence limits 1171–2296 mg/kg
Female rats  1100 mg/kg    95% Confidence limits 785–1540 mg/kg

EXAMPLE 12

The growth-inhibitory activity of 4-chlorophenyl-2-thienyliodonium chloride, trifluoroacetate and trichloroacetate salts against some microorganisms most relevant to the human skin was determined by standard agar dilution tests using conventional nutrient agar for testing bacteria and conventional malt yeast agar for testing fungi and yeasts and wherein the culture medium was free of any additive other than the test compound and water used to dissolve the same. The test plates were incubated at 30°C. for 72 hours. Results are summarized in the following Table.

GROWTH INHIBITORY CONCENTRATIONS 4-CHLOROPHENYL-2-THIENYLIODONIUM:

| Concentration ppm, agar basis | Chloride Bacteria Sa* | St | Aa | Pa | Fungi, Yeasts Ca | Tm | Pd | T | Trifluoroacetate Bacteria Sa | St | Aa | Pa | Fungi, Yeasts Ca | Tm | Pd | T | Trichloroacetate Bacteria Sa | St | Aa | Pa | Fungi, Yeasts Ca | Tm | Pd | T |
|---|---|---|---|---|---|---|---|---|---|---|---|---|---|---|---|---|---|---|---|---|---|---|---|---|
| 100 | − | − | − | − | − | − | ∓ | − | − | − | − | − | ∓ | − | ∓ | − | − | − | − | − | − | − | ∓ | − |
| 75  | − | − | − | − | − | − | ∓ | − | − | − | − | − | ∓ | − | ± | − | − | − | − | − | ∓ | − | + | − |
| 50  | − | − | − | − | ± | − | + | − | − | − | − | − | + | − | + | − | − | − | − | − | + | − | + | − |
| 25  | − | − | − | − | + | − | + | ± | − | − | − | − | + | − | + | + | − | − | − | − | + | − | + | + |
| 10  | − | − | − | − | + | − | + | + | − | − | − | − | + | − | + | + | − | − | − | − | + | − | + | + |
| 7.5 | − | − | − | − | + | − | + | + | − | − | − | − | + | − | + | + | − | − | − | − | + | − | + | + |
| 5.0 | − | − | − | − | + | − | + | + | − | − | − | − | + | − | + | + | − | − | − | − | + | − | + | + |
| 2.5 | − | − | − | − | + | − | + | + | − | − | − | − | + | − | + | + | − | − | − | ∓ | + | − | + | + |
| 1.0 | + | ∓ | ∓ | ∓ | + | − | + | + | + | ∓ | + | + | + | − | + | + | ∓ | + | ± | + | − | + | + | + |
| Untreated control | + | + | + | + | + | + | + | + | | | | | | | | | | | | | | | | |

*Rating:
+ = growth   ± = greater than 50% reduction of growth   ∓ = greater than 90% reduction of growth   − = no growth
Sa = S. aureus
Ca = C. albicans
St = S. typhosa
Tm = T. mentagrophytes
Aa = A. aerogenes
Pd = P. digitatum
Pa = P. aeruginosa
T = Trichoderma Species Madison P-42

What is claimed is:

1. A germicidal detergent composition for controlling microbes of the group consisting of bacteria, fungi and yeasts comprising an anionic, nonionic or mixture of an anionic and a nonionic detergent and an antimicrobial amount of 4-chlorophenyl-2-thienyliodonium chloride, trifluoroacetate or trichloroacetate salt.

2. The germicidal detergent of claim 1 wherein the active agent is 4-chlorophenyl-2-thienyliodonium chloride.

* * * * *

UNITED STATES PATENT AND TRADEMARK OFFICE
CERTIFICATE OF CORRECTION

PATENT NO. : 3,944,498
DATED : March 16, 1976
INVENTOR(S) : Clarence L. Moyle

It is certified that error appears in the above-identified patent and that said Letters Patent are hereby corrected as shown below:

Column 1, line 68, "S. typhose," should read --S. typhosa--;

Columns 9, 11 and 13, Table 2, Compound Nos. 1 thru 16, "⊖" should read --⊕--;

Column 13, "A. ANTIMICROBIAL ACTIVITY" should read --B. ANTIMICROBIAL ACTIVITY--;

Columns 15 and 16, Table 2, Compound Nos. 3 thru 11, "⊖" should read --⊕--;

Column 15, Table 2, Compound Nos. 1 and 2, above I insert ⊕;

Column 17, Table 2, Compound No. 12 should read:

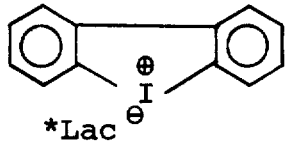

Column 17, Table 2, Compound Nos. 13, 14 and 15, "⊖" should read --⊕--;

Column 19, line 52, "ClPhThICL:" should read --ClPhThICl:--.

Signed and Sealed this

Twenty-eighth Day of September 1976

[SEAL]

Attest:

RUTH C. MASON
Attesting Officer

C. MARSHALL DANN
Commissioner of Patents and Trademarks